United States Patent [19]
Fukushima et al.

[11] Patent Number: 5,637,787
[45] Date of Patent: Jun. 10, 1997

[54] GAS CHROMATOGRAPH

[75] Inventors: Toyoaki Fukushima, Kyoto; Syoji Masanao, Osaka, both of Japan

[73] Assignee: Shimadzu Corporation, Japan

[21] Appl. No.: 667,329

[22] Filed: Jun. 20, 1996

Related U.S. Application Data

[63] Continuation of Ser. No. 427,402, Apr. 24, 1995, abandoned.

[30] Foreign Application Priority Data

May 31, 1994 [JP] Japan .................. 6-142322

[51] Int. Cl.$^6$ .................. G01N 30/02
[52] U.S. Cl. .................. 73/23.35; 73/23.42
[58] Field of Search .................. 73/23.35, 23.41, 73/23.42, 23.38

[56] References Cited

U.S. PATENT DOCUMENTS

| | | | |
|---|---|---|---|
| 3,112,639 | 12/1963 | Maxwell | 73/23.42 |
| 3,119,251 | 1/1964 | Bowers | 73/23.42 |
| 3,150,517 | 9/1964 | Kuffer et al. | 73/23.42 |
| 3,447,360 | 6/1969 | Laseter | 73/23.35 |
| 4,587,834 | 5/1986 | Fisher | 73/23.1 |
| 4,732,581 | 3/1988 | Cheh et al. | 55/67 |
| 5,049,509 | 9/1991 | Szakasits et al. | 73/23.8 |
| 5,468,643 | 11/1995 | Su et al. | 73/61.55 X |

Primary Examiner—Hezron E. Williams
Assistant Examiner—Jay L. Politzer
Attorney, Agent, or Firm—Majestic, Parsons, Siebert & Hsue

[57] ABSTRACT

A gas chromatograph has a switch valve for selectably directing an incoming carrier gas into a first flow route for split analyses or into a second flow route for direct injection analyses. A pressure sensor and a bypass flow route with low flow resistance connected to the carrier gas supply route are also connected to the switch valve. When the switch valve is set for a split analysis, the pressure sensor becomes connected to a vaporization chamber through a flow route with low flow resistance. When the switch valve is set for a direct injection analysis, the pressure sensor becomes connected to the carrier gas supply route through the bypass flow route.

8 Claims, 2 Drawing Sheets

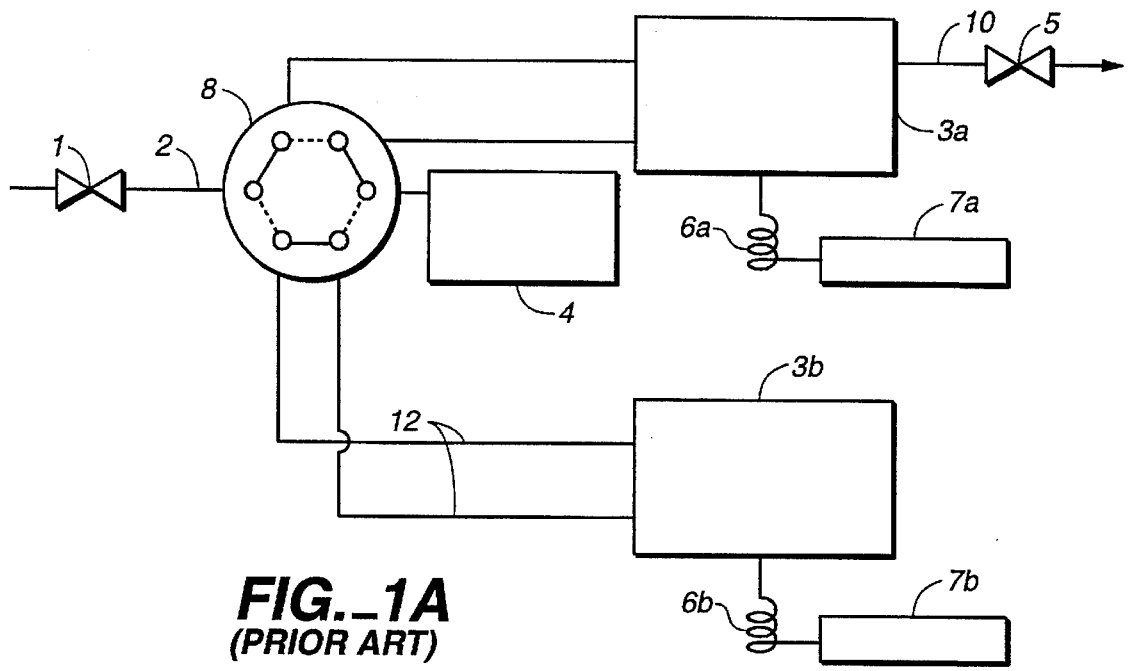
FIG._1A
(PRIOR ART)
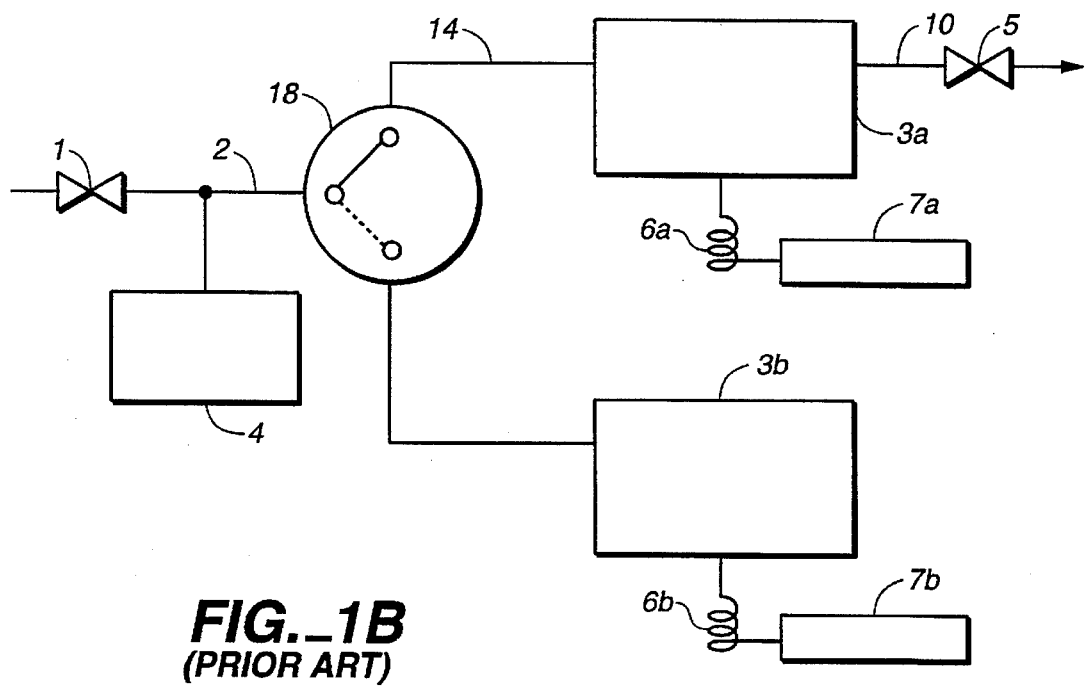
FIG._1B
(PRIOR ART)

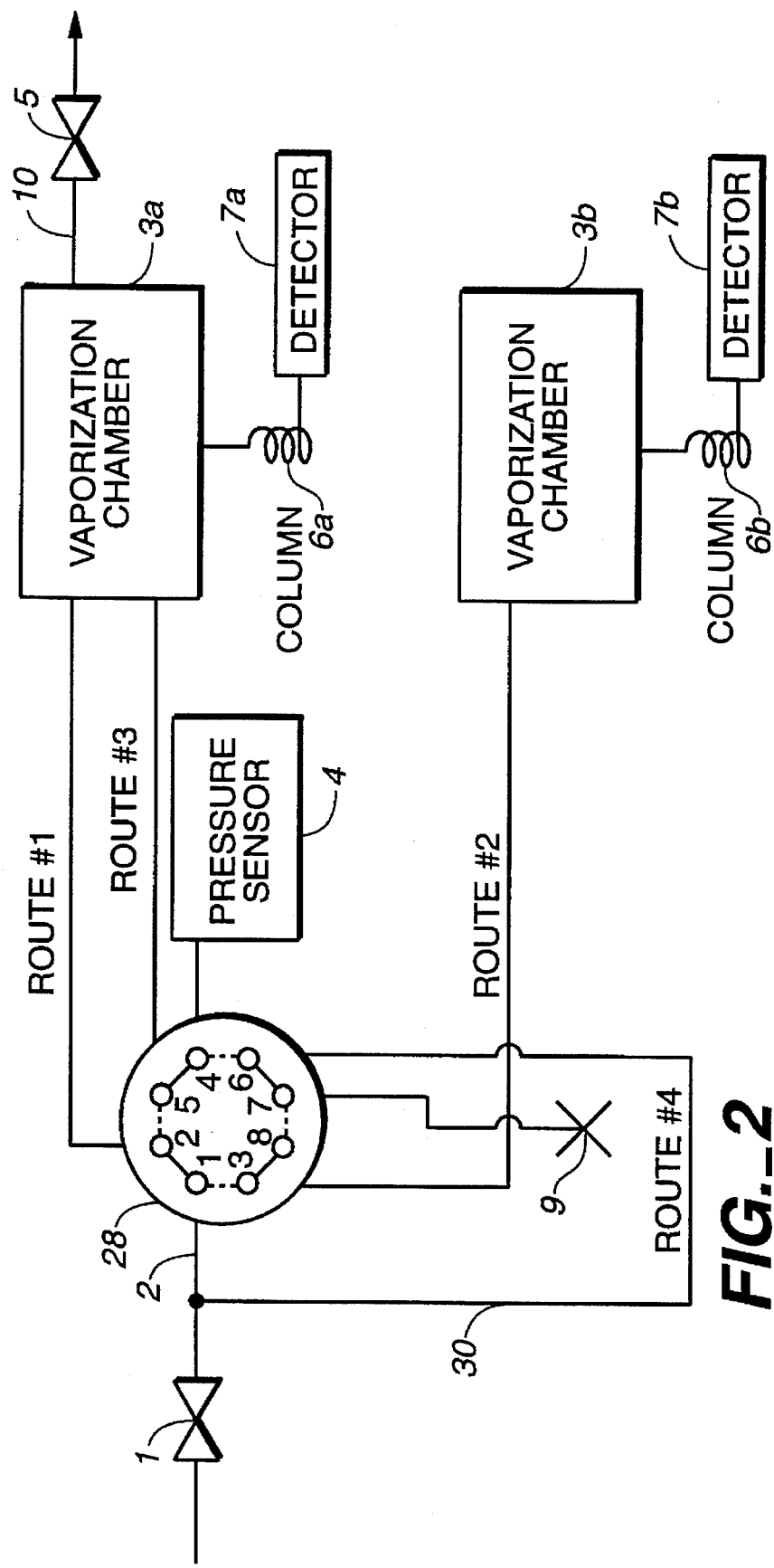
FIG._2

GAS CHROMATOGRAPH

This is a continuation of application Ser. No. 08/427,402, filed Apr. 24, 1995, now abandoned.

BACKGROUND OF THE INVENTION

This invention relates to a gas chromatograph used for the analysis of various chemical substances and, more particularly, to a gas chromatograph provided with both a vaporization chamber for split analyses and another vaporization chamber for direct injection analyses such that selectably both split and direct injection analyses can be carried out.

Prior art gas chromatographs adapted to be used selectably for both split and direct injection analyses by switching flow routes are generally provided with, as shown in FIGS. 1A and 1B, a first flow route connected to a first vaporization chamber $3a$ for split analyses connected to a column $6a$ provided with a detector $7a$ and a discharge flow route 10 provided with a carrier gas discharge valve 5, and a second flow route connected to a second vaporization chamber $3b$ for direct injection analyses connected to another column $6b$ with a detector $7b$, as well as a carrier gas supply route 2 including a carrier gas supply valve 1 for adjusting the flow rate of the carrier gas through a carrier gas supply route 2, a pressure sensor 4 and a switch valve 8 or 18 for selectably connecting the carrier gas supply route 2 to the vaporization chamber $3a$ for split analyses or the vaporization chamber $3b$ for direct injection analyses. When a split analysis is carried out, the carrier gas discharge valve 5 in the discharge flow route 10 is adjusted according to the output from the pressure sensor 4 in order to adjust the pressure inside the vaporization chamber $3a$. When a direct injection analysis is carried out, the carrier gas supply valve 1 is adjusted according to the output from the pressure sensor 4.

When the prior art gas chromatograph shown in FIG. 1A is used for a split analysis, its switch valve 8 is in the position indicated by solid lines in FIG. 1A such that the carrier gas is introduced into the vaporizer chamber $3a$ for split analyses, a portion of it being discharged through the discharge flow route 10 and the rest being led into the column $6a$. In the meantime, the carrier gas discharge valve 5 is controlled by the output from the pressure sensor 4 such that a desired proportion of the carrier gas supplied through the carrier gas supply valve 1 will be discharged. It will be assumed that the flow resistance between the pressure sensor 4 and the carrier gas discharge valve 5 is small enough to be negligible. When this chromatograph is used for a direct injection analysis, on the other hand, the switch valve 8 is switched to the position indicated by dotted lines in FIG. 1A such that the carrier gas supplied through the carrier gas supply valve 1 is introduced entirely into the vaporization chamber $3b$ and from there into the column $6b$ for direct injection analyses. The carrier gas supply valve 1 is controlled in this case by the output from the pressure sensor 4, but an accurate control becomes difficult due to a temporal phase difference which occurs between the action of the carrier gas supply valve 1 and the pressure change detected by the pressure sensor 4 because of the flow resistance inside the carrier gas supply route 2 and the direct injection flow route (indicated by numeral 12) between the switch valve 8 and the vaporization chamber $3b$ as well as the volume of the vaporization chamber $3b$.

The prior art gas chromatograph shown in FIG. 1B is different in that its pressure sensor 4 is inserted on the upstream side between the carrier gas supply valve 1 and its switch valve 18. When this gas chromatograph is used for a direct injection analysis, its switch valve 18 is set as shown by a dotted line such that the carrier gas flows entirely through the vaporization chamber $3b$ into the column $6b$ for direct injection analyses. There is no problem in this situation because the carrier gas supply valve 1 is controlled by the output from the pressure sensor 4. When this gas chromatograph is used for a split analysis, on the other hand, the switch valve 18 is set as shown by the solid line in FIG. 1B such that the carrier gas is introduced into the vaporization chamber $3a$ for split analyses and the carrier gas discharge valve 5 is controlled by the output from the pressure sensor 4. In this situation, however, an accurate control becomes difficult due to a temporal phase difference which occurs between the action of the carrier gas discharge valve 5 and the pressure change detected by the pressure sensor 4 because of the flow resistance inside the carrier gas supply route 2, the split flow route (indicated by numeral 14) and the discharge flow route 10 as well as the volume of the vaporization chamber $3a$.

Prior art gas chromatograph apparatus for both split and direct injection analyses were formed as shown either in FIG. 1A or in FIG. 1B. Thus, either the control in direct injection analyses or control and accuracy in split injection analyses had to be compromised if use is made of a prior art gas chromatograph as described above.

SUMMARY OF THE INVENTION

It is therefore an object of this invention to provide a gas chromatograph capable of controlling the pressure inside vaporization chambers both for split and direct injection analyses such that accurate analyses are possible in both types of analyses.

An improved gas chromatograph embodying the present invention, with which the above and other objects can be accomplished, may be characterized as comprising a new switch valve adapted to connect a pressure sensor to the vaporization chamber for split analyses through a low-resistance flow route when the carrier gas supply route is connected to this vaporization chamber, and to the carrier gas supply route through another low-resistance flow route when the carrier gas supply route is connected to the vaporization chamber for direct injection analyses.

When a split analysis is carried out with a gas chromatograph thus structured, flow resistance is small between the carrier gas discharge valve for controlling the pressure inside the vaporization chamber and the pressure sensor because the pressure sensor is connected to the vaporization chamber through a low-resistance flow route. When it is used for a direct injection analysis, on the other hand, flow resistance is small between the carrier gas supply valve for controlling the pressure inside the vaporization chamber and the pressure sensor because the pressure sensor is connected to the carrier gas supply route through another low-resistance flow route. Thus, there is no problem in the pressure control for either split or direct injection analyses.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIGS. 1A and 1B are schematic flow route diagrams of prior art gas chromatographs; and FIG. 2 is a schematic flow route diagram of a gas chromatograph embodying this invention.

Throughout herein, components of gas chromatographs that are substantially equivalent to each other are indicated by the same numerals and not repetitiously explained.

DETAILED DESCRIPTION OF THE INVENTION

FIG. 2 shows a gas chromatograph according to one embodiment of the invention, many components of which are substantially identical to those explained above with reference to prior art gas chromatographs shown in FIGS. 1A and 1B and are indicated by the same numerals. A carrier gas supply route 2 containing a carrier gas supply valve 1 is connected to a switch valve 28 (at Port #1), to which are also connected a vaporization chamber 3a (thorugh "a first flow route at Port #2) for split analyses and another vaporization chamber 3b for direct injection analyses. The vaporization chamber 3a for split analyses is connected to a column 6a and a discharge flow route 10 for discharging a part of the carrier gas therethrough. A detector 7a is connected to the outlet of the column 6a and a carrier gas discharge valve 5 for controlling the pressure inside the vaporization chamber 3a is connected in the discharge flow route 10. The vaporization chamber 3b for direct injection analyses is connected to another column 6b having another detector 7b connected to its outlet.

The switch valve 28 is further connected to a pressure sensor 4 (the Port #4) and a bypass flow route 30 (or a fourth flow route, at Port #6) connected to the carrier gas supply route 2 at the other end. When the switch valve 28 is in the position shown by solid lines in FIG. 2, the carrier gas from the carrier gas supply route 2 is directed to the vaporization chamber 3a (through Ports #1 and #2) for split analyses, and the pressure sensor 4 becomes connected to the vaporization chamber 3a through a low-resistance flow route (or a third flow route, connected to Port #5 of the switch valve). When the switch valve 28 is in the position shown by dotted lines in FIG. 2, the carrier gas from the carrier gas supply route 2 is directed to the vaporization chamber 3b for direct injection analyses through Ports #1 and #3 and a "second flow route, and the pressure sensor 4 becomes connected through the bypass flow route 30 to the carrier gas supply route 2.

An eight-port valve may be used as the switch valve 28 with one of the ports (Port #7) blocked as symbolically illustrated by numeral 9 such that the bypass 30 will be closed when the switch valve 28 is switched for a split analysis. Another port (Port #8) remains unrelated to the operation of the valve 28.

When this gas chromatograph is used for a split analysis, the switch valve 28 is set as shown by the solid lines in FIG. 2 such that the carrier gas supply route 2 is connected to the vaporization chamber 3a for split analyses and a downstream section of the vaporization chamber 3a becomes connected to the pressure sensor 4 through a flow route having low flow resistance. The carrier gas discharge valve 5 is controlled by the output from the pressure sensor 4. Since the pressure sensor 4 is thus adapted to measure the pressure near the inlet of the column 6a, or somewhere downstream of the inlet, the carrier gas discharge valve 5 can be controlled with improved reliability.

When this gas chromatograph is used for a direct injection analysis, the switch valve 28 is set as shown by the broken lines in FIG. 2 such that the carrier gas supplied through the carrier gas supply valve 1 is directed to the vaporization chamber 3b for direct injection analyses and the pressure sensor 4 becomes connected to the carrier gas supply route 2 through the bypass 30 having low flow resistance. Since the pressure sensor 4 is thus adapted to measure the pressure inside the carrier gas supply route 2 upstream of the column 6b, the carrier gas supply valve 1 can be controlled with improved reliability.

In summary, simultaneously as the gas chromatograph of this invention is switched for a split analysis or a direct injection analysis, the pressure sensor is connected to a position of pressure measurement either near or downstream of the inlet of the column or upstream of the column inlet such that the control of the vaporization chamber becomes easier and accurate measurements become possible in the case of a split analysis and the pressure control becomes easier in the case of a direct injection analysis.

What is claimed is:

1. A gas chromatograph comprising:

a first flow route including a first vaporization chamber connected to a first column for split analyses, a discharge flow route including a carrier gas discharge valve being connected to said first vaporization chamber;

a second flow route including a second vaporization chamber for direct injection analyses;

a carrier gas supply flow route containing a carrier gas supply valve for controlling the flow rate of a carrier gas;

a pressure sensor; and a switch valve means for selectably connecting said carrier gas supply flow route to said first vaporization chamber to thereby cause said pressure sensor to be connected to said first vaporization chamber through a third flow route or to said second vaporization chamber to thereby cause said pressure sensor to be connected directly to said carrier gas supply flow route through a fourth flow route and to remain disconnected from said second vaporization chamber.

2. The gas chromatograph of claim 1 wherein said switch valve means has a first port connected to said carrier gas supply flow route, a second port connected to said first flow route, a third port connected to said second flow route, a fourth port connected to said pressure sensor, a fifth port connected to said third flow route, and a sixth port connected to said fourth flow route.

3. The gas chromatograph of claim 2 wherein said switch valve means can be selectably in a first position wherein said first port is connected to said second port and said fourth port is connected to said fifth port or in a second position wherein said first port is connected to said third port and said fourth port is connected to said sixth port.

4. The gas chromatograph of claim 1 wherein said third and fourth flow routes have negligible flow resistance.

5. The gas chromatograph of claim 2 wherein said third and fourth flow routes have negligible flow resistance.

6. The gas chromatograph of claim 3 wherein said third and fourth flow routes have negligible flow resistance.

7. A gas chromatograph comprising:

an eight-port switch valve having first through eighth ports and being adapted to be selectably either in a first position wherein said first and second ports are connected, said third and eighth ports are connected, said fourth and fifth ports are connected, said sixth and seventh ports are connected and no other pair of said ports is connected together, or a second position wherein said first and third ports are connected, said second and fifth ports are connected, said fourth and sixth ports are connected, said seventh and eighth ports are connected and no other pair of said ports is connected together, said seventh port being blocked;

a first flow route connected to said second port, said first flow route including a first vaporization chamber connected to a first column for split analyses, a discharge flow route including a carrier gas discharge valve being connected to said first vaporization chamber;

a second flow route connected to said third port, said second flow route including a second vaporization chamber for direct injection analyses;

a carrier gas supply flow route connected to said first port, said carrier gas supply flow route containing a carrier gas supply valve for controlling the flow rate of a carrier gas;

a pressure sensor connected to said fourth port;

a third flow route connecting said fifth port with said first vaporization chamber; and a fourth flow route connecting said sixth port with said carrier gas supply flow route.

8. The gas chromatograph of claim 7 wherein said third and fourth flow routes have negligible flow resistance.

* * * * *